United States Patent
Friend et al.

[11] Patent Number: 5,415,645
[45] Date of Patent: May 16, 1995

[54] RETRACTABLE SHEATH FOR HYPODERMIC NEEDLE

[76] Inventors: John M. Friend, 1634 Kerns Road, Burlington, Ontario, Canada, L7P 3H1; William C. Friend, Box 77 Site 7, R.R. #1, Calgary, Alberta, Canada, T2P 2G4

[21] Appl. No.: 235,846
[22] Filed: Apr. 29, 1994
[51] Int. Cl.⁶ ............................................. A61M 5/00
[52] U.S. Cl. .................................. 604/110; 604/198; 604/263
[58] Field of Search ............... 604/192, 198, 110, 187, 604/263

[56] References Cited

U.S. PATENT DOCUMENTS

| | | |
|---|---|---|
| 2,876,770 | 3/1959 | White . |
| 4,820,275 | 4/1989 | Haber et al. . |
| 4,840,185 | 6/1989 | Hernandez . |
| 4,861,338 | 8/1989 | Mathiesen et al. . |
| 4,908,023 | 3/1990 | Yuen . |
| 4,911,693 | 3/1990 | Paris . |
| 4,946,446 | 8/1990 | Vadher . |
| 4,966,592 | 10/1990 | Burns et al. . |
| 5,013,301 | 5/1991 | Marotta, Jr. et al. . |
| 5,014,384 | 4/1992 | Parry . |
| 5,061,251 | 10/1991 | Juhasz . |
| 5,104,385 | 4/1992 | Huband ............................ 604/198 |
| 5,106,379 | 4/1992 | Leap . |
| 5,106,380 | 4/1992 | Lobello ............................ 604/263 X |
| 5,147,303 | 9/1992 | Martin . |
| 5,201,708 | 4/1993 | Martin . |
| 5,222,947 | 6/1993 | D'Amico . |
| 5,246,428 | 9/1993 | Falknor . |
| 5,269,761 | 12/1993 | Stehrenberger et al. ....... 604/198 X |

Primary Examiner—John D. Yasko
Attorney, Agent, or Firm—Barrigar & Moss

[57] ABSTRACT

A retractable sheath for a hypodermic needle is shown for preventing accidental needle pricks. The sheath automatically extends to cover the needle and retracts to expose the needle without having to touch the sheath or activate any locking or release mechanisms. A barrel is mounted on the hypodermic needle or syringe with the needle projecting axially therefrom. A telescoping sheath is mounted in or over the barrel to extend and retract respectively to cover and uncover the needle. A cam and cam follower co-operatively formed in the barrel and sheath prevents the sheath from retracting by an accidental force on the sheath but allows the sheath to be cocked, so that a second deliberate force on the sheath allows the sheath to retract allowing the needle to be inserted into the skin. The cam has a first segment which allows the cam follower to slide longitudinally permitting the sheath to retract, a second segment which blocks the cam follower preventing retraction of the sheath, and an intermediate segment that moves the cam follower from the blocked position to the ready or cocked position, so that a subsequent force on the sheath allows it to retract automatically and then return to the blocked position.

15 Claims, 8 Drawing Sheets

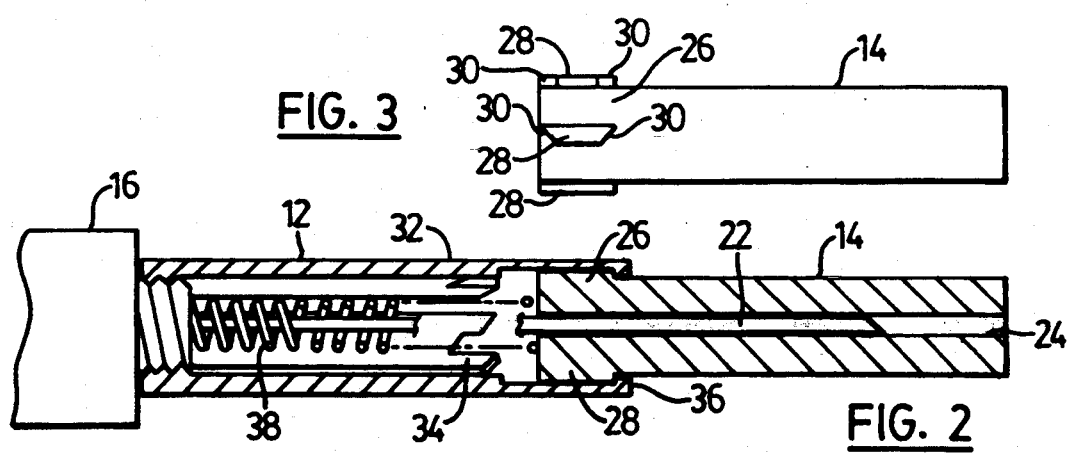
FIG. 3
FIG. 2
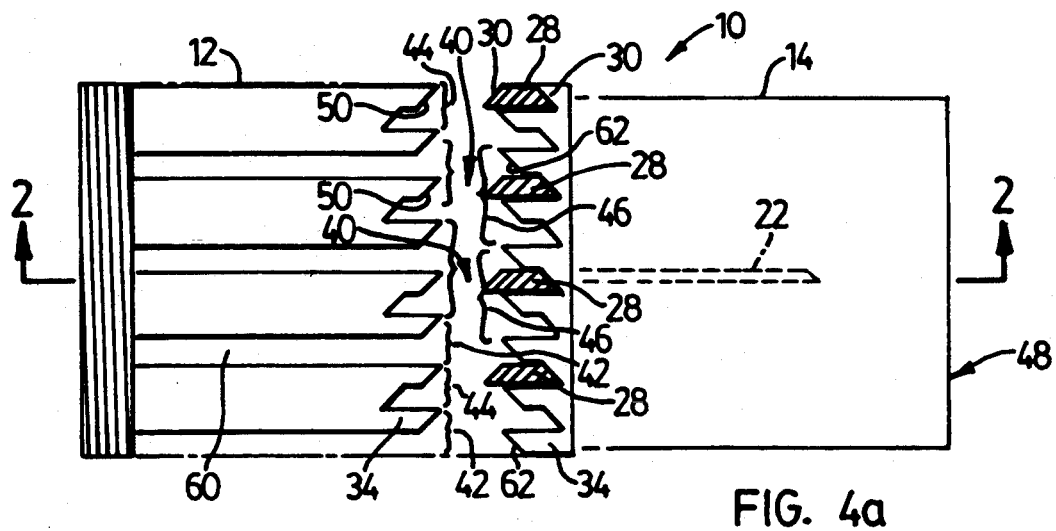
FIG. 4a
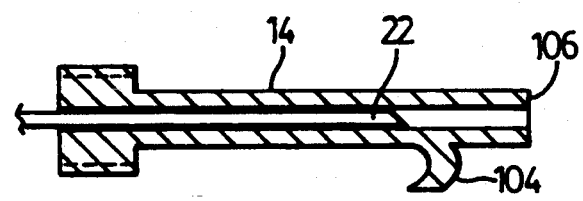
FIG. 7
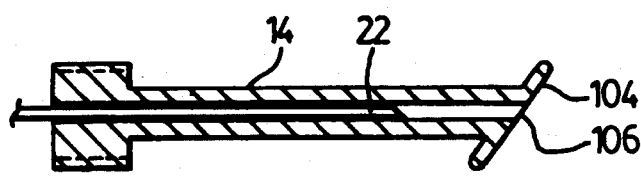
FIG. 8

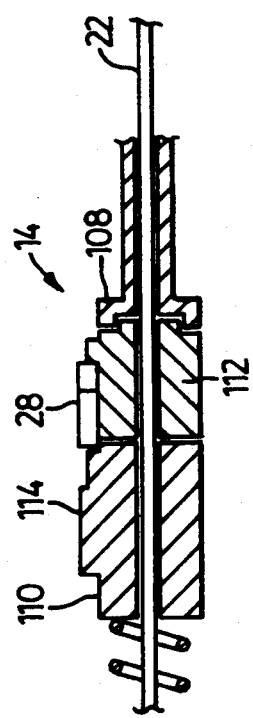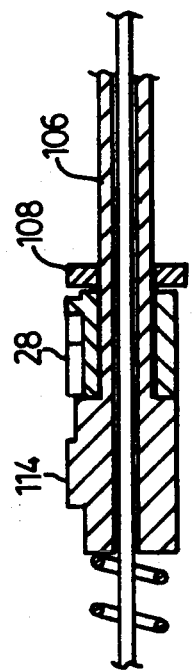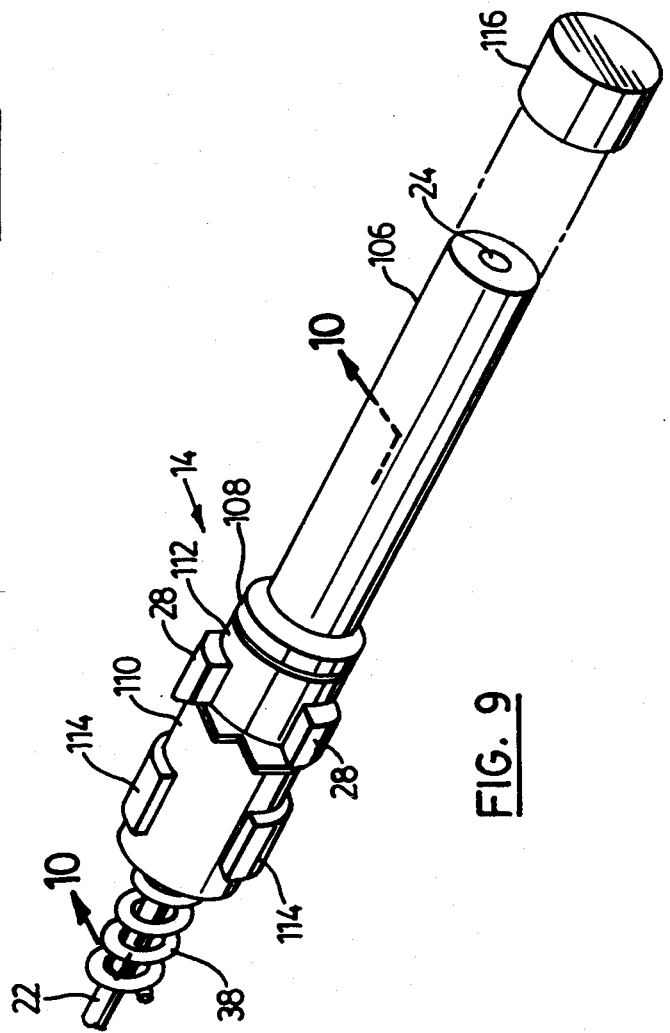

RETRACTABLE SHEATH FOR HYPODERMIC NEEDLE

BACKGROUND OF THE INVENTION

1. Field of the Invention

This invention relates to hypodermic needles, and in particular, to sheathing devices which cover the needle to prevent accidental needle pricks.

2. Description of the Prior Art

It is well known that many very serious diseases, such as Acquired Immune Deficiency Syndrome and Hepatitis can be spread or transmitted by blood or other human or animal bodily fluids. It is a major concern to health care workers who administer medications using hypodermic needles or syringes that the needles, after use on a patient, may accidentally stick or prick the health care worker transmitting a disease from the patient to the health care worker. This can happen, for example, when the patient pulls back suddenly upon insertion or removal of the needle, or when the needles or syringes are being handled for disposal or left protruding from a trash container.

In order to prevent such accidental needle sticks or pricks, many inventions have been made which provide a sheath covering the needle. In some cases, the sheath has to be manually removed or replaced over the needle. This is totally unacceptable, because it is very easy to stab or stick oneself in the hand trying to remove or replace the sheath. In other cases, the sheath is slidably mounted on the syringe to uncover and cover the needle. Bias means are often employed to urge the sheath into the extended or covering position. While this is an improvement over a manually removable sheath, in almost all cases, some type of locking or latching mechanism is employed to retain the sheath either in the retracted or extended position, and this locking mechanism again must be manually actuated with the hand or fingers exposing the hand to accidental pricks while manipulating the mechanism. Further, if the sheath is locked in the retracted position exposing the needle, there is no protection at all to the health care worker from accidental pricks caused by a patient suddenly pulling back or moving violently.

SUMMARY OF THE INVENTION

In this invention, a retractable sheath is telescopically located in a barrel to be mounted on a syringe covering the syringe needle. A cam and cam follower in the sheath and barrel automatically prevents the sheath from retracting until a force on the sheath moves it from a safe position to a ready or cocked position where a subsequent force on the sheath makes it retract exposing the needle, after which the needle again automatically returns to the safe position.

According to one aspect of the invention, there is provided a retractable sheath assembly for hypodermic needle comprising a barrel adapted to be attached to a syringe of a hypodermic needle with the needle projecting axially from the barrel. An elongate, cylindrical sheath is telescopically mounted relative to the barrel and slidably moveable from an extended position to cover the needle to a retracted position uncovering the needle. The sheath has an inner end portion and the barrel has a distal end portion. A cam is formed on one of the barrel distal end portion and the sheath inner end portion. A cam follower is formed on the other of the sheath inner end portion and the barrel distal end portion, the cam follower being adapted to engage the cam. Also, the cam has a first segment unblocking the cam follower and permitting retraction of the sheath to uncover the needle, a second segment blocking the cam follower and preventing retraction of the sheath to uncover the needle, and an intermediate segment for moving the cam follower between the first and second segments after retraction of the sheath to uncover the needle.

According to another aspect of the invention, there is provided a method for preventing accidental syringe needle pricks. The method comprises the steps of providing a sheath covering the syringe needle. The sheath is moved from a first position where the needle is covered and the sheath cannot be retracted to expose the needle, to an intermediate position while keeping the sheath covered. The sheath is subsequently moved to a second position where the needle is uncovered. Also, the sheath is returned to the first position before the needle is again uncovered.

BRIEF DESCRIPTION OF THE DRAWINGS

Preferred embodiments of the invention will now be described, by way of example, with reference to the accompanying drawings, in which:

FIG. 2 is a vertical sectional view of the assembled retractable sheath assembly as shown in FIG. 1;

FIG. 3 is a side elevational view of the sheath of the assembly shown in FIG. 1;

FIG. 4a is a plan view of the inside of the barrel of the sheath assembly of FIG. 1, showing the barrel as if it were unrolled;

FIG. 7 is a vertical sectional view of another embodiment of the sheath;

FIG. 8 is a vertical sectional view of yet another embodiment of the sheath;

FIG. 9 is a perspective view of yet another embodiment of the sheath where the sheath does not rotate during use;

FIG. 10 is a vertical sectional view taken along lines 10—10 of FIG. 9; and

FIG. 11 is a vertical sectional view similar to FIG. 10 showing a modification of the structure of FIG. 10.

DESCRIPTION OF THE PREFERRED EMBODIMENTS

Figure 1:
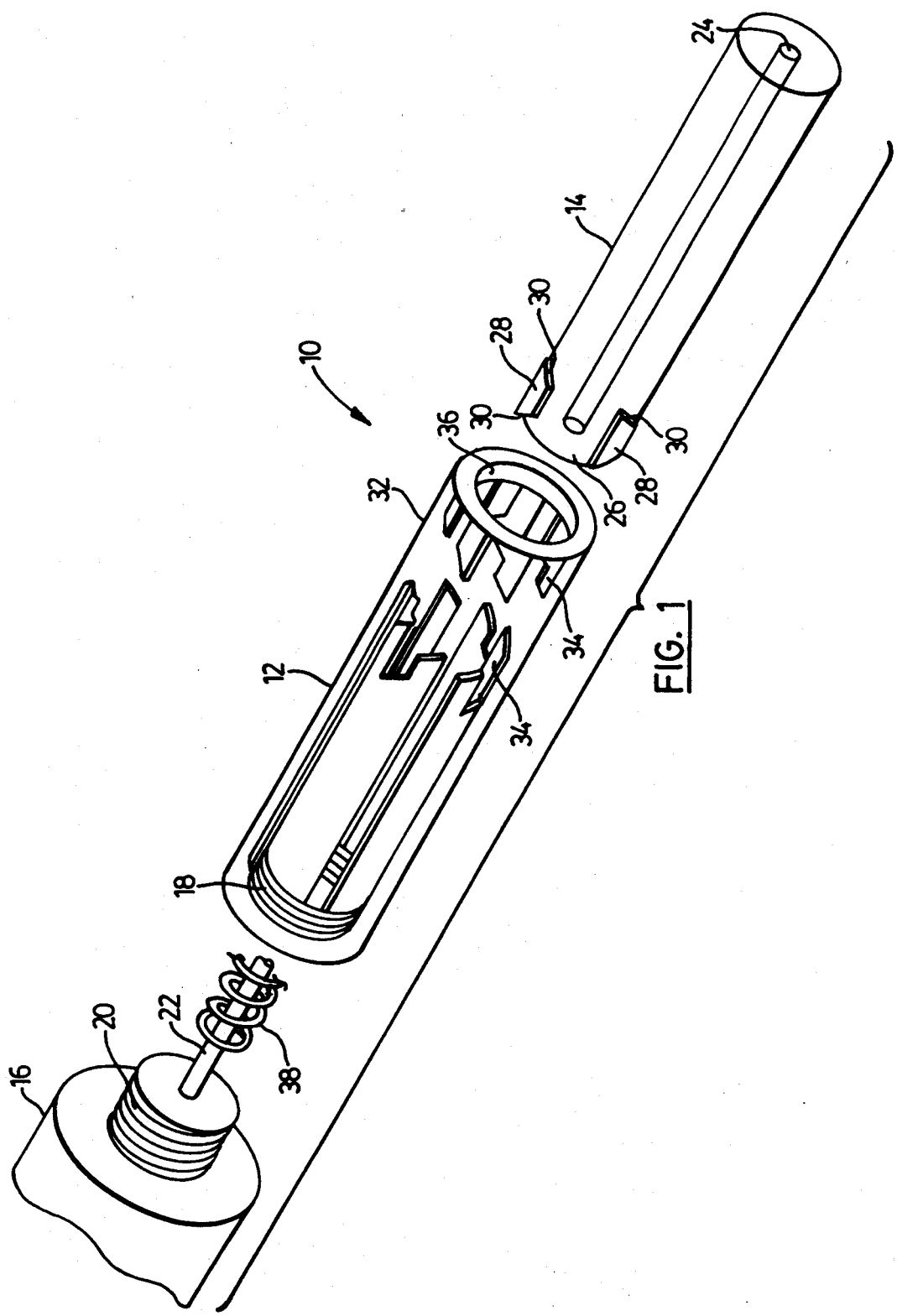
FIG. 1 is a perspective, exploded view of a preferred embodiment of a retractable sheath assembly according to the present invention.

Referring firstly to, FIGS. 1 to 3, a preferred embodiment of a retractable sheath assembly for a hypodermic needle is generally represented by reference numeral 10. Sheath assembly 10 includes a barrel 12 and an elongate, cylindrical sheath 14 telescopically mounted in barrel 12. Barrel 12 is attached to a hypodermic needle or syringe 16 by a female thread 18, and barrel 12 is screwed onto a male thread 20 on syringe 16. It will be appreciated that other forms of connection may be made between barrel 12 and syringe 16, such as a press fit or a bayonet connection. These types of connections are conventional in syringes. The type of connection and the syringe itself are not considered to be part of the present invention, so will not be described in further detail, as long as it is understood that there is some means in barrel 12 to attach sheath assembly 10 to the syringe. Syringe 16 includes a hypodermic needle 22 which is shown broken off in FIG. 1 for the purposes of illustration, but as indicated in FIG. 2, needle 22 extends well into sheath 14 when the sheath is extended as shown in FIG. 2. Again, there are many configurations for needle 22. These needles can be detachable or replaceable or permanently mounted in syringe 16, as will be the case with a disposable syringe 16. Sheath assembly 10 is dimensioned to be compatible with the size and type of needle 22 as will be appreciated by those skilled in the art.

As seen best in FIG. 2 sheath 14 is telescopically or slidably mounted in barrel 12 and has an axial opening 24 to slidably accommodate needle 22 projecting axially from barrel 12. Sheath 14 has an inner end portion 26 and radially projecting cam followers 28 are formed on inner end portion 26. Cam followers 28 are formed with longitudinally opposed, transversely disposed ramps 30, the purpose of which will be described further below.

Barrel 12 has a distal end portion 32 and a cam 34 is formed in distal end portion 32 which cam followers 28 engage to control the movement of sheath 14. Distal end portion 32 also has an inwardly extending distal flange 36 which engages cam followers 28 to prevent sheath 14 from coming out of barrel 12. A spring 38 biases or urges sheath 14 toward the extended position as seen in FIG. 2.

Referring next to FIG. 4a, the inside surfaces of sheath assembly 10 are diagrammatically shown as if it were slit longitudinally and unrolled or developed as if it were flattened. Cam followers 28 of sheath 14 are shown superimposed on cams 34 and cam followers 28 have been cross-hatched for the purposes of clarity. Needle 22 is shown in dotted lines to show its relative position with respect to sheath 14. Cam 34 is made up of four repetitions or cam sets generally indicated by reference numerals 40 to match or correspond with the four cam followers 28 on sheath 14. Each cam set 40 includes a first segment 42 which unblocks cam followers 28 and permits the retraction of sheath 14 to uncover needle 22. Each cam set 40 also includes a second segment 44 which blocks cam followers 28 and prevents retraction of sheath 14 to uncover needle 22. Each cam set 40 also includes an intermediate segment 46 for moving the cam followers 28 between the first and second segments 42, 44 after retraction of sheath 14 to uncover needle 22.

Figure 4B:
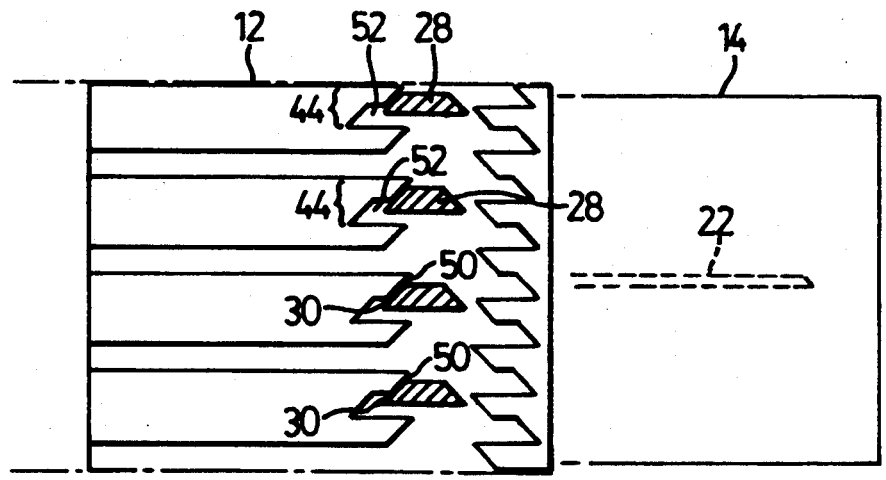
FIGS. 4b through 4g are a series of views similar to FIG. 4a showing schematically the movement of the sheath in the barrel.
Figure 4C:
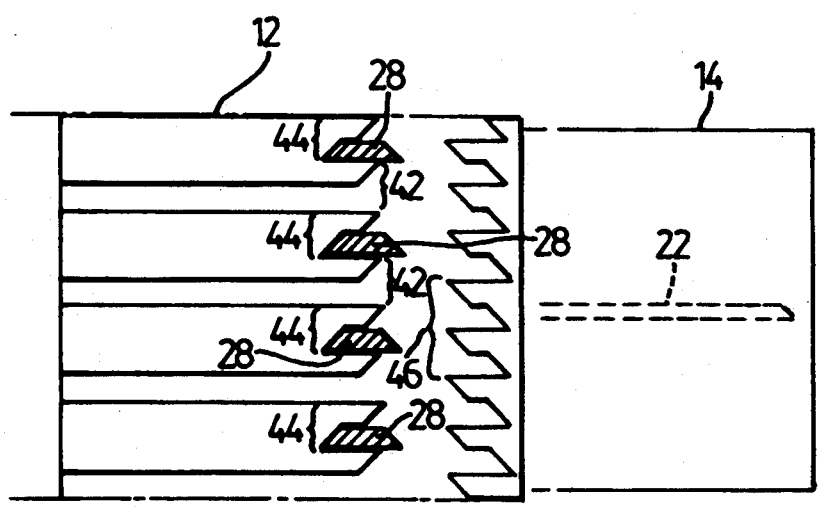

Referring next to FIGS. 4a through 4g, the operation of sheath assembly 10 will now be described. FIG. 4a shows sheath assembly 10 in its starting position as it would be received by a health care worker from the manufacturer or distributer of health care supplies. In this position, cam followers 28 are located in intermediate segments 46 and sheath assembly 10 is in the uncocked or safe position. When a force is applied to the end of sheath 14 as indicated by arrow 48, sheath 14 begins to retract into barrel 12 as shown in FIG. 4b. As seen in FIG. 4b, cam followers 28 approach second segments 44, whereupon ramps 30 engage transversely disposed ramps 50 which direct cam followers 28 into short grooves 52 in second segments 44 as indicated in FIG. 4c. In this position, it will be noted that needle 22 still does not project from the end of sheath 14, so that if an accidental force has caused sheath 14 to move as indicated in FIGS. 4a to 4c, needle 22 would not be exposed and there could not be an accidental needle prick.

Figure 4D:
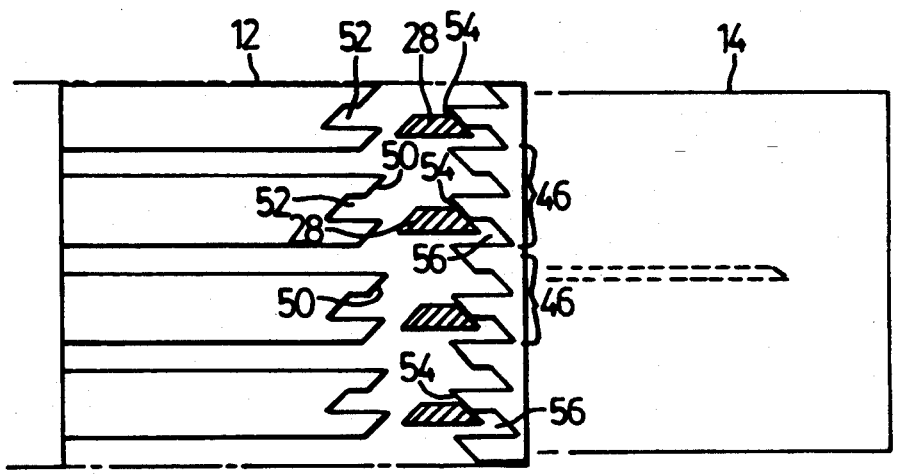
Figure 4E:
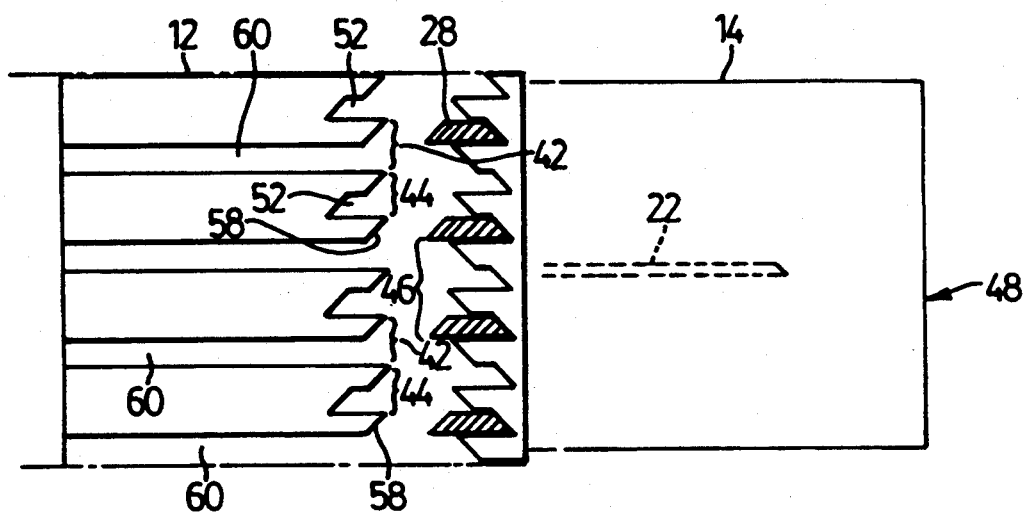

When the pressure is removed from the end of sheath 14, spring 38 causes sheath 14 to move toward the extended position as indicated in FIG. 4d. Cam followers 28 then engage transversely disposed ramps 54 in intermediate segments 46. Ramps 54 are located longitudinally opposed to short grooves 52 and direct cam followers 28 into short grooves 56 in intermediate segments 46 as indicated in FIG. 4e. Each time cam followers 28 hit ramps 50 or 54, this tends to rotate sheath 14 and move or direct the cam followers unidirectionally toward first or second cam segments 42, 44 as the case may be.

Figure 4F:
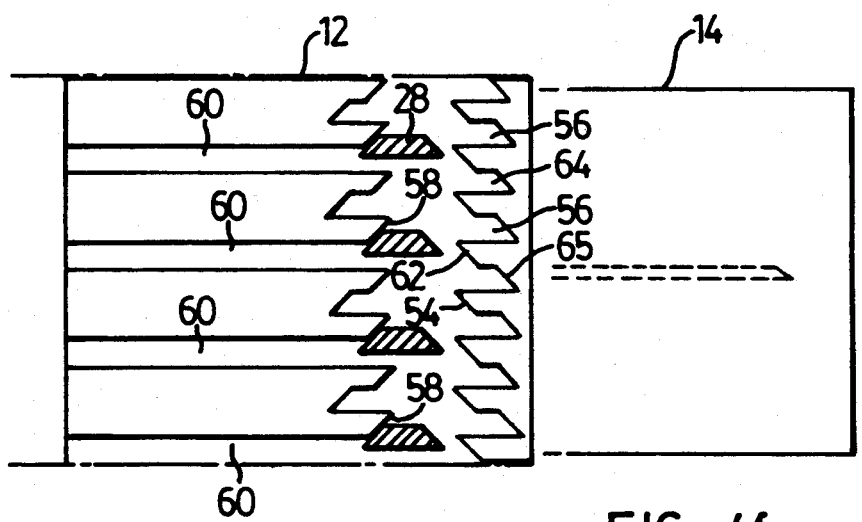
Figure 4G:
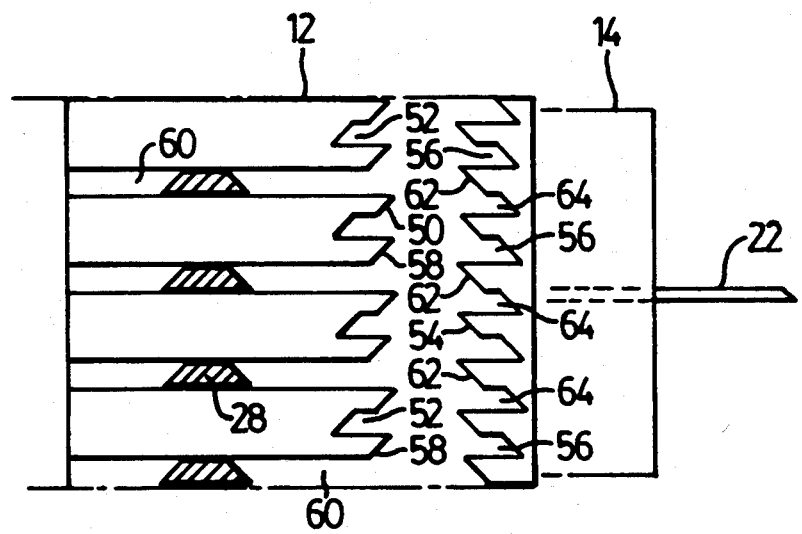

When sheath assembly 10 is in the position shown in FIG. 4e, it is cocked or ready to expose needle 22. A force in the direction of arrow 48 caused, for example, by pressing sheath 14 against the skin at the location where it is desired to insert needle 22, causes sheath 14 to retract inside barrel 12. Cam followers 28 move towards first segments 42 to engage transversely disposed ramps 58, which in turn direct cam followers 28 into long grooves 60 as indicated in FIG. 4f. Cam followers 28 then slide along long grooves 60 allowing sheath 14 to fully retract exposing needle 22 as shown in FIG. 4g.

When it is desired to withdraw needle 22 from the skin, syringe 16 is pulled back and spring 38 causes sheath 14 to again move toward the extended position covering needle 22. Cams 28 engage further transversely disposed ramps 62 causing cam followers 28 to move into further short grooves 64 in intermediate segments 46 to once again place sheath assembly 10 in the position shown in FIG. 4a. At this point, the sheath is in the safe position and cannot accidentally be retracted by, for example, hitting the end of sheath 14 against the hand or body of a health care worker. The cycle can be repeated, if desired.

From the above, it will be seen that cam first segments 42 unblock cam followers 28 and permit the retraction of sheath 14 to uncover needle 22. Second segments 44 block cam followers 28 and prevent retraction of sheath 14 to uncover needle 22. Also, intermediate segments 46 move cam followers 28 between the first and second segments 42, 44 after the retraction of sheath 14 to uncover needle 22.

Figure 5A:
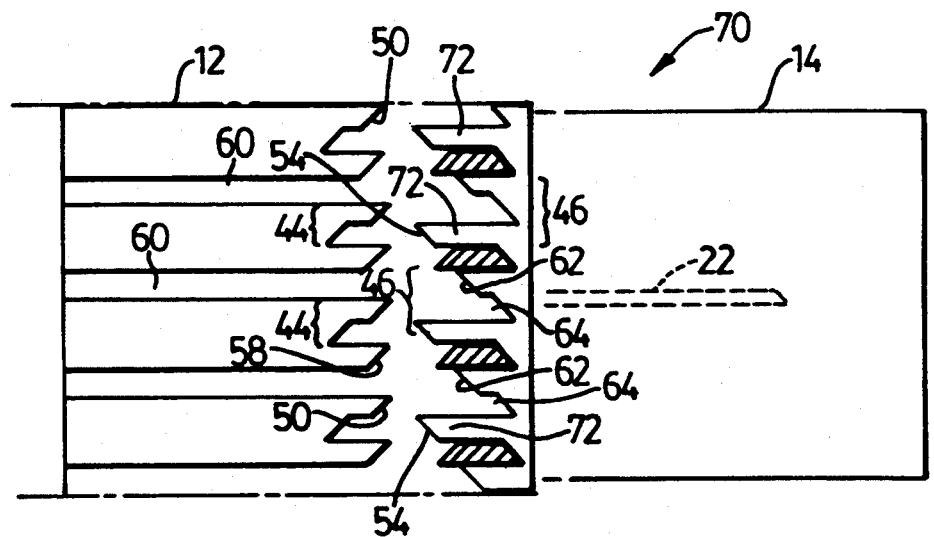
FIGS. 5a and 5b are similar to FIGS. 4a through 4g but show another "single-shot" embodiment where the retraction of the sheath is not repeatable.

Referring next to FIG. 5a, a sheath assembly 70 is shown which is similar to sheath assembly 10, except that intermediate cam segments 46 include an extended leg 72, so that after sheath 14 is retracted to expose needle 22 and cam followers 28 enter short grooves 64, sheath 14 cannot thereafter be retracted to expose needle 22, because cam followers 28 engage ramps 50 and cannot rotate or move down past extended legs 72. This type of sheath assembly is used for intravenous procedures, such as for drips, taking blood samples or donations, etc. Extended legs 72 act as stops to prevent further rotation of sheath 14 after cam followers 28 engage second segments 44 making sheath assembly 70 a "one-shot" device.

Figure 5B:
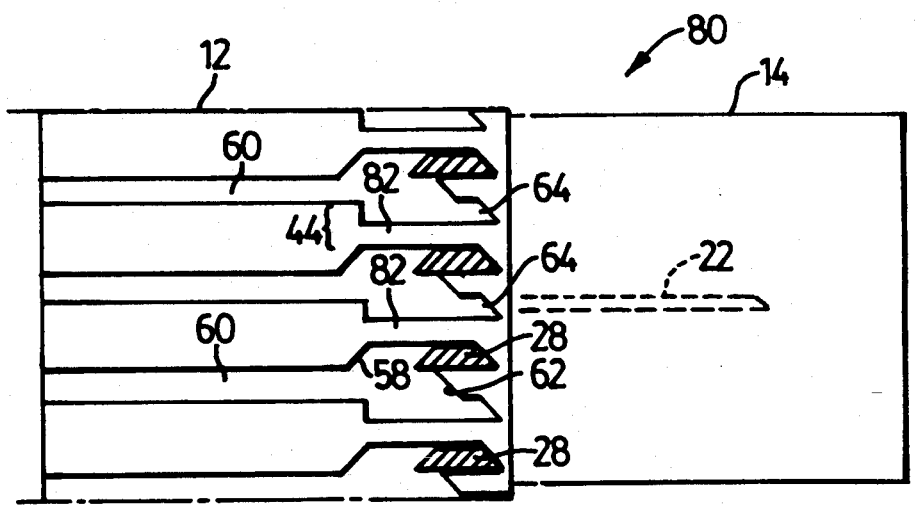

FIG. 5b shows another embodiment of a sheath assembly 80 which is similar to sheath assembly 70 of FIG. 5a except that extended legs 82 extend all the way over to second segments 44. Again, sheath assembly 80 is a "one-shot" device in which the sheath 14 is permitted to retract only once. When syringe 16 is pulled back to withdraw needle 22 from the skin, or if the patient pulls back suddenly or violently, sheath 14 will automatically move into the extended position covering needle 22 preventing the needle from again being exposed if sheath 14 hits another object, such as a health care worker's hand or body.

Figure 6A:
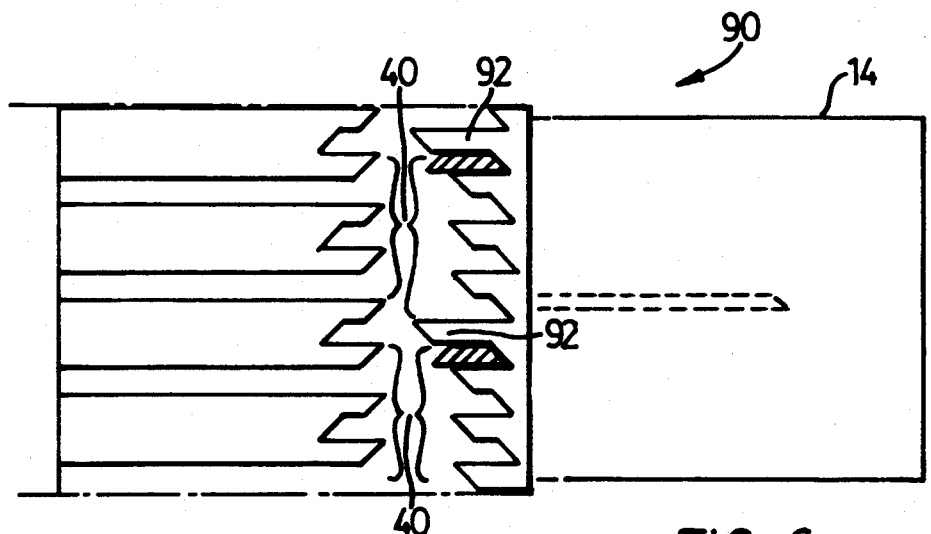
FIGS. 6a and 6b are similar to FIGS. 5a and 5b, but showing a "two-shot" embodiment where the sheath movement is repeated only once.
Figure 6B:
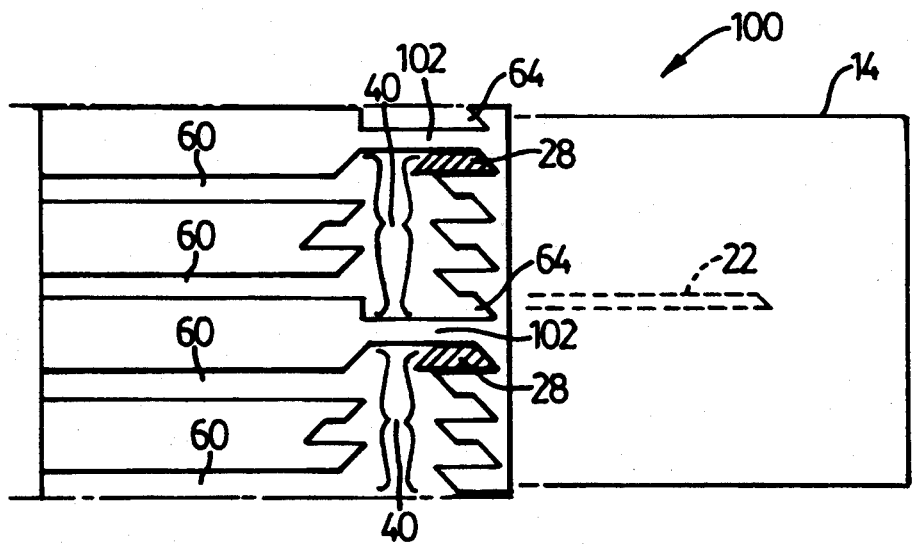

Referring next to FIGS. 6a and 6b, sheath assemblies 90 and 100 are shown which are similar to respective sheath assemblies 70 and 80 of FIGS. 5a and 5b. However, sheath assemblies 90, 100, have two cam sets 40 between each extended leg 92, 102. This produces a "two-shot" device wherein sheath 14 can be retracted a first time, for example to fill syringe 16 with medication. Sheath 14 then returns to the extended uncocked position upon withdrawal of needle 22 from the supply of medication. Further force or pressure on the end of sheath 14 causes it to go into the cocked position similar to that shown in FIG. 4e. Subsequent force or pressure on the end of sheath 14, such as by pressing sheath 14 against the skin at a location where it is desired to make an injection, causes sheath 14 to retract allowing needle 22 to penetrate the skin. Further withdrawal of syringe 16 causes cam followers 28 to enter short grooves 64, and extended legs 82 prevent further rotation and retraction of sheath 14.

FIGS. 7 and 8 show modifications to sheath 14 wherein transverse projections 104 are provided to assist in retracting sheath 14. Since sheath 14 is retracted by pushing the outer distal end portion 106 thereof against the skin, transverse projections 104 prevent sheath 14 from sliding along the skin, especially where a low angle of attack is made for the injection as in the case where it is desired to insert needle 22 just below the surface of the skin.

Referring next to FIGS. 9 and 10, a modification to sheath 14 is shown in which the sheath inner end portion includes an annular flange 108, a distal inner portion 110 and an intermediate portion 112 rotatably located between annular flange 108 and distal inner portion 110. Cam followers 28 are formed on rotatable intermediate portion 112. Distal inner portion 110 has radially disposed ribs 114 which are located in long grooves 60 complete with integral intermediate cam segments similar to intermediate segments 46 for moving the cam followers 28 between the first and second segments 42, 44 after retraction of sheath 14 to uncover needle 22. In this modification, intermediate cam segments 46 would not be necessary in the distal end portion 32 of barrel 12, as they had been transferred to the distal inner portion 110 of sheath 14. As sheath 14 reciprocates or slides in and out of barrel 12, intermediate portion 112 rotates, but the sheath outer distal end portion 106 and distal inner portion 110 do not.

FIG. 11 is a slight modification to the embodiment shown in FIGS. 9 and 10 in that sheath outer distal end portion 106 and distal inner portion 110 are formed integrally and intermediate portion 112 is an annular member. An optional separate annular flange 108 is attached to outer distal end portion 106 to hold intermediate portion 112 in position. It will be appreciated that the transverse projections 104 shown in FIGS. 7 and 8 can be used with the embodiments shown in FIGS. 9 to 11.

It will be noted that an end cap 116 is shown in FIG. 9 to cover the end of outer distal end portion 106. Such an end cap can be used with any of the embodiments shown in FIGS. 1 to 11. End cap 116 prevents foreign matter or germs from entering axial opening 24 and is also useful to be used before disposing of disposable sheath 16 in the trash in the multiple exposure embodiments of sheath assembly 10, thus ensuring that there will not be any accidental exposures of the needle 22 when handling this trash.

The sheath assemblies of the present invention are formed of suitable plastic material. Sheath 14 is preferably made transparent, so that a health care worker can see the progress of needle 22 as it is emerging from sheath 14 to make sure that it is positioned where desired for an injection.

To summarize the method of preventing accidental syringe needle pricks using the sheath assemblies of the present invention, a needle sheath is provided which covers the needle. This sheath is initially in a first position where the needle is covered and the needle cannot be retracted to expose the needle, because the sheath cam followers hit a cam intermediate segment. This does, however, move the sheath into an intermediate or cocked position while keeping the sheath covered. Subsequent force on the sheath, such as by pressing it against the skin, moves the sheath to a second or retracted position uncovering the needle. As soon as the syringe or needle is withdrawn, the sheath automatically again covers the needle and it cannot again be uncovered accidentally, such as by the sheath hitting another object, such as a health care worker's hand or body.

It will be apparent to those skilled in the art that in light of the foregoing disclosure, many alterations and modifications are possible in the practise of this invention without departing from the spirit or scope thereof. Accordingly, the scope of the invention is to be construed in accordance with the substance defined in the following claims.

What is claimed is:

1. A retractable sheath assembly for a hypodermic needle, comprising:
   a barrel adapted to be attached to a syringe of a hypodermic needle with the needle projecting axially from the barrel;
   an elongate, cylindrical sheath telescopically mounted relative to the barrel and slidably moveable from an extended position to cover the needle to a retracted position uncovering the needle;
   the sheath having an inner end portion and the barrel having a distal end portion;
   a cam formed on one of said barrel distal end portion and said sheath inner end portion;
   a cam follower formed on the other of said sheath inner end portion and said barrel distal end portion, the cam follower being adapted to engage the cam; and
   the cam having a first segment unblocking the cam follower and permitting retraction of the sheath to uncover the needle, a second segment blocking the cam follower and preventing retraction of the sheath to uncover the needle, and an intermediate segment for moving the cam follower between the first and second segments after retraction of the sheath to uncover the needle.

2. A retractable sheath assembly as claimed in claim 1 wherein the cam first segment includes a longitudinal groove and a transversely disposed ramp for directing the cam follower into said groove for movement therealong to retract the sheath.

3. A retractable sheath assembly as claimed in claim 2 wherein the cam intermediate segment includes a transversely disposed ramp located longitudinally opposite to said groove for directing the cam follower toward the cam second segment upon extension of the sheath.

4. A retractable sheath assembly as claimed in claim 3 and further comprising means for biasing the sheath toward the extended position.

5. A retractable sheath assembly as claimed in claim 4 wherein the cam is formed on the barrel and the cam follower is formed on the sheath.

6. A retractable sheath assembly as claimed in claim 4 wherein the cam second segment is disposed longitudinally opposite to said intermediate segment, so that a force tending to retract the sheath after the cam engages the said intermediate segment causes the cam follower to engage the second segment preventing the needle from being uncovered.

7. A retractable sheath assembly as claimed in claim 3 wherein the first segment, second segment and intermediate segment form a cam set, and further comprising a second cam set identical to and located adjacent to the first cam set, and wherein the first cam set second segment includes a transversely disposed ramp located longitudinally opposite to the first cam set intermediate segment for directing the cam follower toward the second cam set first segment upon extension of the sheath away from the first cam set second segment.

8. A retractable sheath assembly as claimed in claim 6 wherein said ramps are oriented to cause the sheath to rotate unidirectionally, and wherein the cam further comprises a stop to prevent rotation of the sheath after the cam follower engages the second segment.

9. A retractable sheath assembly as claimed in claim 7 wherein said ramps are oriented to cause the sheath to rotate unidirectionally, and wherein the cam further comprises a stop to prevent rotation of the sheath after the cam follower engages the second segment of the second cam set.

10. A retractable sheath assembly as claimed in claim 5 wherein the sheath inner end portion includes an annular flange, a distal inner portion and an intermediate portion rotatably located between the annular flange and the distal inner portion, the cam follower being formed on the intermediate portion.

11. A retractable sheath assembly as claimed in claim 5 wherein the barrel has an inner peripheral wall, and wherein the cam first segment, second segment and intermediate segment form a cam set formed in said inner peripheral wall, and further comprising a plurality of identical cam sets located circumferentially around the inner peripheral wall of the barrel, and wherein the sheath inner end portion includes a plurality of cam followers, one said cam follower being associated with each cam set.

12. A retractable sheath assembly as claimed in claim 4 wherein the cam follower is formed with longitudinally opposed, transversely disposed ramps adapted to matingly engage the first and intermediate segment ramps.

13. A retractable sheath assembly as claimed in claim 11 wherein there are four equi-spaced cam sets and cam followers in said sheath assembly.

14. A retractable sheath assembly as claimed in claim 1 wherein the sheath is transparent.

15. A retractable sheath assembly as claimed in claim 1 wherein the sheath has an outer distal end portion including a transverse projection.

* * * * *